United States Patent
Hu et al.

(10) Patent No.: US 9,636,296 B2
(45) Date of Patent: *May 2, 2017

(54) METHODS OF REDUCING HAIR LOSS AND/OR FACILITATING HAIR GROWTH AND/OR REGROWTH

(71) Applicant: JOHNSON & JOHNSON CONSUMER INC., Skillman, NJ (US)

(72) Inventors: Longsheng Hu, Piscataway, NJ (US); Virginia Streusand Goldman, Morris Plains, NJ (US); Josephine A. Minerva, Parsippany, NJ (US); Susan Wendling, Annandale, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/511,621

(22) Filed: Oct. 10, 2014

(65) Prior Publication Data

US 2015/0025097 A1 Jan. 22, 2015

Related U.S. Application Data

(60) Continuation of application No. 13/908,507, filed on Jun. 3, 2013, now Pat. No. 8,871,773, which is a division of application No. 12/638,142, filed on Dec. 15, 2009, now Pat. No. 8,470,880.

(51) Int. Cl.
| | | |
|---|---|---|
| *A61K 31/20* | (2006.01) | |
| *A61K 8/97* | (2017.01) | |
| *A61K 8/36* | (2006.01) | |
| *A61K 8/67* | (2006.01) | |
| *A61K 8/92* | (2006.01) | |
| *A61Q 7/00* | (2006.01) | |
| *A61K 31/19* | (2006.01) | |
| *A61K 8/365* | (2006.01) | |
| *A61K 8/49* | (2006.01) | |
| *A61K 31/505* | (2006.01) | |
| *A61K 31/201* | (2006.01) | |

(52) U.S. Cl.
CPC .............. *A61K 8/97* (2013.01); *A61K 8/36* (2013.01); *A61K 8/365* (2013.01); *A61K 8/4953* (2013.01); *A61K 8/678* (2013.01); *A61K 8/922* (2013.01); *A61K 31/19* (2013.01); *A61Q 7/00* (2013.01); *A61K 31/20* (2013.01); *A61K 31/201* (2013.01); *A61K 31/505* (2013.01); *A61K 2800/522* (2013.01); *A61K 2800/592* (2013.01); *Y10S 514/88* (2013.01)

(58) Field of Classification Search
CPC ...... A61K 13/19; A61K 31/34; A61K 31/355; A61K 31/505; A61K 31/20; A61K 31/201
USPC ................. 514/256, 558, 560, 880
See application file for complete search history.

(56) References Cited

U.S. PATENT DOCUMENTS

| | | | |
|---|---|---|---|
| 4,874,794 A | 10/1989 | Katz | |
| 4,912,111 A * | 3/1990 | Sank | A61K 31/505 514/256 |
| 5,520,918 A | 5/1996 | Smith | |
| 5,652,274 A | 7/1997 | Martin | |
| 5,658,956 A | 8/1997 | Martin et al. | |
| 5,834,510 A | 11/1998 | Yu et al. | |
| 6,051,602 A | 4/2000 | Bissett | |
| 6,207,694 B1 | 3/2001 | Murad | |
| 6,284,234 B1 | 9/2001 | Niemiec et al. | |
| 6,419,913 B1 | 7/2002 | Niemiec et al. | |
| 6,495,498 B2 | 12/2002 | Niemiec et al. | |
| 6,762,158 B2 | 7/2004 | Lukenbach et al. | |
| 6,858,202 B2 | 2/2005 | Niemiec et al. | |
| 6,908,889 B2 | 6/2005 | Niemiec et al. | |
| 7,049,331 B2 | 5/2006 | Eisinger et al. | |
| 7,074,747 B1 | 7/2006 | Lukenbach et al. | |
| 7,262,158 B1 | 8/2007 | Lukenbach et al. | |
| 7,273,847 B2 | 9/2007 | McCormack, Jr. | |
| 7,351,739 B2 | 4/2008 | Ho et al. | |
| 7,357,923 B1 | 4/2008 | Vasquez Lipi | |
| 7,452,527 B2 | 11/2008 | Murad | |
| 8,470,833 B2 * | 6/2013 | Hu | A61K 8/361 514/256 |
| 8,871,773 B2 * | 10/2014 | Hu | A61K 8/36 514/256 |
| 8,927,554 B2 * | 1/2015 | Hu | A61K 8/361 514/256 |
| 2003/0068297 A1 | 4/2003 | Jain | |
| 2003/0176303 A1 | 9/2003 | Niemiec et al. | |
| 2008/0069779 A1 | 3/2008 | Tamarkin et al. | |
| 2008/0076828 A1 | 3/2008 | Dalton et al. | |
| 2008/0145331 A1 | 6/2008 | Bruning | |
| 2008/0206159 A1 | 8/2008 | Tamarkin et al. | |
| 2009/0068160 A1 | 3/2009 | Castiel et al. | |
| 2009/0087462 A1 | 4/2009 | Trembley et al. | |
| 2009/0117146 A1 | 5/2009 | Khan et al. | |

FOREIGN PATENT DOCUMENTS

| | | |
|---|---|---|
| DE | 3133132 A1 | 3/1983 |
| DE | 3246265 | 6/1984 |
| DE | 4113346 | 10/1992 |
| FR | 2167407 | 8/1973 |
| FR | 2569347 | 2/1986 |
| FR | 2909870 A1 | 6/2008 |
| GB | 2341317 | 3/2000 |
| JP | 3167111 | 7/1991 |
| JP | 04-108721 | 4/1992 |
| JP | 04-338319 | 11/1992 |
| JP | 2000/038340 | 2/2000 |
| JP | 2002/080328 | 3/2002 |
| JP | 2003-073268 | 3/2003 |
| RU | 2034532 C1 | 5/1995 |
| WO | 9717953 | 5/1997 |
| WO | 2007/099398 | 9/2007 |
| ZA | 9505409 A | 4/1997 |

OTHER PUBLICATIONS

Science of Cosmetic Oils and Fats, $2^{nd}$ Print, Apr. 10, 2001, p. 7-31 (English Translation of portions of pp. 8 and 9 and Table 2-14 on p. 27).
Journal of Dermatological Science, Miyamoto I., Hamada K., vol. 10, No. 1, pp. 99-99(1), Jul. 1995.
Guide for the Care and Use of Laboratory Animals, NIH Publication No. 85-23.

* cited by examiner

Primary Examiner — Kevin E Weddington

(57) ABSTRACT

The present disclosure relates to methods of retarding hair loss or facilitating hair growth and/or regrowth. More specifically, the present disclosure relates to methods of using the disclosed compositions to increase the rate of terminal hair growth and/or regrowth in a mammal.

1 Claim, No Drawings

METHODS OF REDUCING HAIR LOSS AND/OR FACILITATING HAIR GROWTH AND/OR REGROWTH

CROSS-REFERENCE TO RELATED APPLICATIONS

The present application is a continuation of U.S. patent application Ser. No. 13/908,507, filed Jun. 3, 2013, which application is a divisional of U.S. patent application Ser. No. 12/638,142, filed Dec. 15, 2009, the entirety of which applications are hereby incorporated by reference herein as if fully set forth herein.

TECHNICAL FIELD

The present disclosure relates to methods of retarding hair loss or facilitating hair growth and/or regrowth. More specifically, the present disclosure relates to methods of using the disclosed compositions to increase the rate of terminal hair growth in a mammal.

BACKGROUND OF THE PRESENT INVENTION

Alopecia, or hair loss, in its various forms is an ongoing problem afflicting mankind and animals. Men, woman and children can all suffer from alopecia, which can result of one, or a combination of, of factors including genetic factors, hormonal factors, surgery, trauma and stress. The universality of the occurrence of alopecia has led to continuing efforts throughout history to discover compositions for stimulating hair growth and preventing hair loss.

A number of "natural" remedies for alopecia based solely on herbs and plant extracts have been proposed. However, such compounds have proved to have very little if any effect.

Accordingly, an aspect of the present invention is to provide a method for reducing hair loss and facilitate hair growth and/or regrowth and/or providing a thicker or richer hair coat.

Another aspect of the present disclosure is concerned with methods of using compositions comprising at least one acid, at least one antioxidant and a select fatty acid mixture.

Another aspect of the present disclosure is concerned with using the disclosed compositions to accelerate the onset of the anagen phase of hair growth in a mammal.

A still further aspect of the present disclosure is concerned with using the disclosed compositions to increase the rate at which terminal hair appears on the skin of a mammal.

Still other objects and advantages of the present disclosure will become readily apparent by those skilled in the art from the following detailed description, wherein it is shown and described only in the preferred embodiments, simply by way of illustration of the best mode. As will be realized, the disclosure is capable of other and different embodiments, and its several details are capable of modifications in various obvious respects, without departing from the spirit of the disclosure. Accordingly, the description is to be regarded as illustrative in nature and not as restricted.

SUMMARY OF THE INVENTION

According to the present disclosure, methods are provided for reducing hair loss and/or facilitating hair growth or hair regrowth. More specifically, the methods of this disclosure exhibit enhanced ability to decrease hair loss and/or promote hair growth or regrowth.

In one embodiment, the present disclosure relates to a composition comprising
  a. a safe and effective amount of at least one hair growth or regrowth active; and
  b. from about 0.1% to about 99%, optionally from about 5% to about 50%, and optionally from about 10% to about 40%, optionally from about 15% to about 30%, by weight of the composition of an admixture, comprising:
     i. from 0.01% to 99.98%, or optionally 10% to 90%, or optionally from 20% to 70%, or optionally from 25% to 50% or optionally from 30% to 40%, or optionally about 33%, by weight of the admixture of an acid selected from the group consisting of intermediates of the Kreb cycle, a non-Kreb cycle intermediate alpha keto acid, derivatives thereof and mixtures thereof;
     ii. optionally, from 0.01% to 99.98%, or optionally 10% to 90%, or optionally from 20% to 70%, or optionally from 25% to 50% or optionally from 30% to 40%, or optionally about 33%, by weight of the admixture of an antioxidant; and
     iii. from 0.01% to 99.98%, or optionally 10% to 90%, or optionally from 20% to 70%, or optionally from 25% to 50% or optionally from 30% to 40%, or optionally about 33%, by weight of the admixture of a fatty acid mixture or fatty acid mixture source comprising at least 7, optionally at least 14, and optionally at least 22, unsaturated or saturated fatty acids selected from the group consisting of, but not limited to, butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, gadoleic acid, pentadecanoic acid, margaric acid, margaroleic acid, behenic acid, dihomolinoleic acid, arachidonic acid and lignoceric acid.

In another embodiment, the present disclosure relates to a method of reducing hair loss and/or facilitating hair growth or hair regrowth comprising the steps of applying to skin of a mammal in need of such treatment a safe and effective amount of a composition comprising from about 0.1% to about 100%, optionally from about 5% to about 50%, and optionally from about 10% to about 40%, optionally from about 15% to about 30%, by weight of the composition of an admixture, comprising:
  a. from 0.01% to 99.98%, or optionally 10% to 90%, or optionally from 20% to 70%, or optionally from 25% to 50% or optionally from 30% to 40%, or optionally about 33%, by weight of the admixture of an alpha-keto acid;
  b. from 0.01% to 99.98%, or optionally 10% to 90%, or optionally from 20% to 70%, or optionally from 25% to 50% or optionally from 30% to 40%, or optionally about 33%, by weight of the admixture of an antioxidant; and
  c. from 0.01% to 99.98%, or optionally 10% to 90%, or optionally from 20% to 70%, or optionally from 25% to 50% or optionally from 30% to 40%, or optionally about 33%, by weight of the admixture of a fatty acid mixture or fatty acid mixture source comprising at least 7, optionally at least 14, and optionally at least 22, unsaturated or saturated fatty acids selected from the group consisting of, but not limited to, butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, gadoleic acid, pentadecanoic acid, margaric acid, margaroleic acid, behenic acid, dihomolinoleic acid, arachidonic acid and lignoceric acid.

In another embodiment, the present disclosure relates to a method of reducing hair loss and/or facilitating hair growth and/or regrowth comprising the steps of applying to a scalp in need of such treatment a safe and effective amount of a composition comprising from about 0.1% to about 100%, optionally from about 5% to about 50%, and optionally from about 10% to about 40%, optionally from about 15% to about 30%, by weight of the composition of an admixture, comprising:
  a. from 0.01% to 99.98%, or optionally 10% to 90%, or optionally from 20% to 70%, or optionally from 25% to 50% or optionally from 30% to 40%, or optionally about 33%, by weight of the admixture of an acid selected from the group consisting of pyruvic acid, a salt thereof and mixtures thereof;
  b. from 0.01% to 99.98%, or optionally 10% to 90%, or optionally from 20% to 70%, or optionally from 25% to 50% or optionally from 30% to 40%, or optionally about 33%, by weight of the admixture of a tocopherol or an ester thereof; and
  c. from 0.01% to 99.98%, or optionally 10% to 90%, or optionally from 20% to 70%, or optionally from 25% to 50% or optionally from 30% to 40%, or optionally about 33%, by weight of the admixture of a fatty acid mixture source, the fatty acid mixture source being an oil mixture comprising:
    1 from 0.01% to 99.98%, or optionally 10% to 90%, or optionally from 20% to 70%, or optionally from 25% to 50% or optionally from 30% to 40%, or optionally about 33%, by weight of the fatty acid mixture of olive oil;
    2. from 0.01% to 99.98%, or optionally 10% to 90%, or optionally from 20% to 70%, or optionally from 25% to 50% or optionally from 30% to 40%, or optionally about 33%, by weight of the fatty acid mixture of cocoa butter; and
    3. from 0.01% to 99.98%, or optionally 10% to 90%, or optionally from 20% to 70%, or optionally from 25% to 50% or optionally from 30% to 40%, or optionally about 33%, by weight of the fatty acid mixture of cottonseed oil.

In another embodiment, the present disclosure relates to a method of reducing hair loss and/or facilitating hair growth or hair regrowth comprising the steps of applying to the scalp of a mammal in need of such treatment a safe and effective amount of a composition comprising from about 0.1% to about 100%, optionally from about 5% to about 50%, and optionally from about 10% to about 40%, optionally from about 15% to about 30%, by weight of the composition of an admixture, comprising:
  a. from 0.01% to 99.98%, or optionally 10% to 90%, or optionally from 20% to 70%, or optionally from 25% to 50% or optionally from 30% to 40%, or optionally about 33%, by weight of the admixture of an acid selected from the group consisting of pyruvic acid, a salt thereof and mixtures thereof;
  b. from 0.01% to 99.98%, or optionally 10% to 90%, or optionally from 20% to 70%, or optionally from 25% to 50% or optionally from 30% to 40%, or optionally about 33%, by weight of the admixture of an antioxidant; and
  c. from 0.01% to 99.98%, or optionally 10% to 90%, or optionally from 20% to 70%, or optionally from 25% to 50% or optionally from 30% to 40%, or optionally about 33%, by weight of the admixture of a fatty acid mixture or fatty acid source wherein the ratio of the pyruvic acid component to the fatty acid mixture is from 0.01:1 (or about 0.01:1) to 1:0.01 (about 1:0.01); the ratio of the pyruvic acid component to the antioxidant component is from 0.01:1 (or about 0.01:1) to 1:0.01 (or about 1:1.01); and the ratio of the fatty acid mixture component to the antioxidant component is from 0.01:1 (or about 0.01:1) to 1:0.01 (or about 1:0.01), or, optionally, wherein the ratio of the pyruvic acid component or the fatty acid mixture component to the antioxidant component is from 1:1 (or about 1:1) to 1:0.01 (or about 1:0.01).

In one other embodiment the present invention relates to a composition comprising:
  a. optionally, a safe and effective amount of at least one hair growth or regrowth active;
  b. from 5% (or about 5%) to 10% (or about 10%), optionally from 6% (or about 6%) to about 8% (or about 8%), by weight of the composition of an acid;
  c. from 5% (or about 5%) to 10% (or about 10%), optionally from 6% (or about 6%) to about 8% (or about 8%), by weight of the composition of a antioxidant; and
  d. from 5% (or about 5%) to 10% (or about 10%), optionally from 6% (or about 6%) to about 8% (or about 8%), by weight of the composition of a fatty acid mixture or fatty acid mixture source, the fatty acid mixture or fatty acid mixture source being an oil mixture comprising:
    i) from 0.01% to 99.98%, or optionally 10% to 90%, or optionally from 20% to 70%, or optionally from 25% to 50% or optionally from 30% to 40%, or optionally about 33%, by weight of the fatty acid mixture of a first oil;
    ii) from 0.01% to 99.98%, or optionally 10% to 90%, or optionally from 20% to 70%, or optionally from 25% to 50% or optionally from 30% to 40%, or optionally about 33%, by weight of the fatty acid mixture of a second oil; and
    iii) from 0.01% to 99.98%, or optionally 10% to 90%, or optionally from 20% to 70%, or optionally from 25% to 50% or optionally from 30% to 40%, or optionally about 33%, by weight of the fatty acid mixture of a third oil.

The present disclosure finds application in all mammalian species, including both humans and animals. In humans, the compositions of the present invention can be applied for example, to the head, pubic area, upper lip, eyebrows, and eyelids. In animals raised for their pelts, e.g. mink, the compositions can be applied over the entire surface of the body to improve the overall pelt for commercial reasons. The methods can also be used for cosmetic reasons in animals, e.g. applied to the skin of dogs and cats having bald patches due to mange or other diseases.

Other aspects of the present invention will become readily apparent by those skilled in the art from the following detailed description, wherein it is shown and described only in the preferred embodiments, simply by way of illustration of the best mode. As will be realized, the disclosure is capable of other and different embodiments, and its several details are capable of modifications in various obvious respects, without departing from the spirit of the disclosure. Accordingly, the description is to be regarded as illustrative in nature and not as restricted.

DETAILED DESCRIPTION OF THE INVENTION

The compositions of the present invention can comprise, consist of, or consist essentially of the essential elements and limitations of the invention described herein, as well any of the additional or optional ingredients, components, or limitations described herein.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All documents incorporated herein by reference in their entirety are only incorporated herein to the extent that they are not inconsistent with this specification.

All percentages, parts and ratios are based upon the total weight of the composition of the present invention, unless otherwise specified. All such weights as they pertain to the listed ingredients are based on the active level and, therefore, do not include carriers or by-products that may be included in commercially available materials, unless otherwise specified.

The term "safe and effective amount" as used herein means an amount of a compound or composition such as a topical or system active sufficient to significantly induce a positive benefit, for example, hair growth or regrowth, but low enough to avoid serious side effects, i.e., to provide a reasonable benefit to risk ratio, within the scope of sound judgment of the skilled artisan.

The Admixture

The compositions of the present invention further include an admixture comprising: 1) an acid selected from the group consisting of intermediates of the Kreb cycle, non-Kreb cycle intermediate alpha keto acid, derivatives thereof and mixtures thereof; and/or an antioxidant and 2) a mixture of saturated and unsaturated fatty acids.

In certain embodiments, the admixture is present in the composition at a concentration of from 0.1% (or about 0.1%) to 100% (or about 100%), optionally from 0.1% (or about 0.1%) to 99% (or about 99%), optionally from 3% (or about 3%) to 75% (or about 75%), optionally from 5% (or about 5%) to 50% (or about 50%), optionally from 10% (or about 10%) to 40% (or about 40%), optionally from 15% (or about 15%) to 30% (or about 30%), or optionally from 19% (or about 19%) to 23% (or about 23%), by weight of the composition.

The Acid

In certain embodiments, the acid of the admixture of the present invention is selected from the group consisting of intermediates of the Kreb cycle, non-Kreb cycle alpha keto acids, derivatives thereof and mixtures thereof.

Kreb cycle (or Citric acid cycle) intermediates useful herein, include, but are not limited to, 2-oxoglutarate, fumarate, succinate, oxaloacetate, citrate, cis-aconitate, isocitrate, oxalosuccinate, alpha-ketoglutarate, L-malate, esters thereof, ethers thereof or salts thereof and mixtures thereof.

In other embodiments, the acid is a non-Kreb cycle intermediate alpha-keto acid (or 2-oxoacid). The alpha-keto acid (or 2-oxoacid) has the keto group adjacent to the carboxylic acid. By "non-Kreb cycle intermediate", as used herein, means a chemical, compound or intermediate not produced by the Kreb cycle or Citric Acid cycle. In certain embodiments, suitable non-Kreb cycle alpha-keto acids include, but are not limited to, pyruvic acid (alpha-ketopropionic acid), alpha-ketoisovaleric acid, alpha-ketoisocaproic acid, salts thereof and mixtures thereof. It should be understood, however, that in addition to these alpha-keto acids, the unqualified term "alpha-keto acids" further includes, but is not limited to, alpha ketoglutaric acid.

In certain embodiments the alpha-keto acid useful as the acid is a pyruvic acid. Pyruvic acid suitable for use in the present invention may be selected from the group consisting of pyruvic acid, salts of pyruvic acid, prodrugs of pyruvic acid, and mixtures thereof. In certain embodiments, the salts of pyruvic acid may be alkali salts and alkaline earth salts. In certain embodiments, the pyruvic acid is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, and mixtures thereof.

In other embodiments, the pyruvic acid is selected from the group of salts consisting of sodium pyruvate, potassium pyruvate, magnesium pyruvate, calcium pyruvate, zinc pyruvate, manganese pyruvate, and the like, and mixtures thereof. In still other embodiments, the pyruvic acid is sodium pyruvate.

Without being limited by theory, it is believed that the acid acts as the energy source component for the admixture. In certain embodiments, the acid is present in the composition in an amount of from 0.01% (or about 0.01%) to 99.98% (or about 99.98%), or optionally 10% (or about 10%) to 90% (or about 90%), or optionally from 20% (or about 20%) to 70% (or about 70%), or optionally from 25% (or about 25%) to 50% (or about 50%), or optionally from 30% (or about 30%) to 40% (or about 40%), or optionally about 33%, by weight of the admixture.

Antioxidant

Antioxidants, as mentioned above, are also present as a component of the admixture of the present invention. Generally, antioxidants are substances which inhibit oxidation or suppress reactions promoted by oxygen or peroxides. Without being limited by theory, it is believed that antioxidants, or, optionally, lipid-soluble antioxidants, can be absorbed into the cellular membrane to neutralize oxygen radicals and thereby protect the hair follicles from oxidative damage. In certain embodiments, the antioxidant may be selected from the group consisting of all forms of Vitamin A including lycopene, lutein, retinal and 3,4-didehydroretinal, all forms of carotene such as alpha-carotene, beta-carotene (beta, beta-carotene), gamma-carotene, delta-carotene, all forms of Vitamin C (D-ascorbic acid, L-aseorbic acid), all forms of tocopherol such as Vitamin E (alpha-tocopherol, 3,4-dihydro-2,5,7,8-tetramethyl-2-(4,8,12-trimethyltri-decyl)-2H-1-benzopy ran-6-ol), beta-tocopherol, gamma-tocopherol, delta-tocopherol, tocoquinone, tocotrienol, and Vitamin E esters which readily undergo hydrolysis to Vitamin E such as Vitamin E acetate and Vitamin E succinate, and Vitamin E salts such as Vitamin E phosphate, prodrugs of Vitamin A, carotene, Vitamin C, and Vitamin E, salts of Vitamin A, carotene, Vitamin C, and Vitamin E, and the like, flavonoids and mixtures thereof. Flavonoids useful in the present can be found in U.S. Pat. No. 6,051,602 to Bissett, herein incorporated by reference. In other embodiments, the antioxidant is selected from the group of lipid-soluble antioxidants consisting of Vitamin A, beta-carotene, tocopherol, and mixtures thereof. In still other embodiments, the antioxidant is tocopherol Vitamin E or Vitamin E acetate. In yet other embodiments, the antioxidant is a polyphenol such as resveratrol or epigallocatechin gallate.

In certain embodiments, the antioxidant component is present in the composition in an amount of from 0.01% (or about 0.01%) to 99.98% (or about 99.98%), or optionally 10% (or about 10%) to 90% (or about 90%), or optionally from 20% (or about 20%) to 70% (or about 70%), or optionally from 25% (or about 25%) to 50% (or about 50%), or optionally from 30% (or about 30%) to 40% (or about 40%), or optionally about 33%, by weight of the admixture.

In certain embodiments, the ratio of the acid component to the antioxidant component on a weight/weight basis is from 0.01:1 (or about 0.01:1) to 1:0.01 (or about 1:0.01), optionally from 1:1 (or about 1:1) to 1:0.1 (or about 1:0.1), optionally from 1:1 (or about 1:1) to 1:0.5 (or about 1:0.5).

The Fatty Acid Mixture or Fatty Acid Mixture Source

The admixture of the present invention also contains a mixture of saturated and unsaturated fatty acids, free or bound, or a source of such saturated and unsaturated fatty acids useful in providing a readily available source of nutrients to hair follicles Suitable mixtures of saturated and unsaturated fatty acids may be derived from animal and vegetable fats and waxes, mammalian or fish egg materials, prodrugs of saturated and unsaturated fatty acids useful in the present compositions, and mixtures thereof. The fatty acids in the fatty acid mixture may be in the form of mono-, di-, or triglycerides, or free fatty acids, or mixtures thereof.

In one embodiment, the fatty acid mixture of saturated and unsaturated fatty acids has a composition similar to that of human fat and comprises the following fatty acids: butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, dihomolinoleic acid, arachidonic acid, behenic acid, lignoceric acid and gadoleic acid. Typically, butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, and gadoleic acid are present in the mixture in about the following percentages by weight, respectively: about 0.2%-0.4% butyric acid, about 0.1% caproic acid, about 0.3%-0.8% caprylic acid, about 2.2%-3.5% capric acid, about 0.9%-5.5% lauric acid, about 2.8%-8.5% myristic acid, about 0.1%-0.6% myristoleic acid, about 23.2%-24.6% palmitic acid, about 1.8%-3.0% palmitoleic acid, about 6.9%-9.9% stearic acid, about 36.0%-36.5% oleic acid, about 20%-20.6% linoleic acid, about 7.5-7.8% linolenic acid, about 1.1%-4.9% arachidic acid, about 2%-3% dihomolinoleic acid, about 7%-9% arachidonic acid, about 3%-4% behenic acid, about 11%-13% lignoceric acid and about 3.3%-6.4% gadoleic acid.

In another embodiment, the fatty acid mixture of saturated and unsaturated fatty acids has a composition similar to chicken fat and comprising the following fatty acids: lauric acid, myristic acid, myristoleic acid, pentadecanoic acid, palmitic acid, palmitoleic acid, margaric acid, margaroleic acid, stearic acid, oleic acid, linoleic acid, linolenic acid, arachidic acid, and gadoleic acid. Optionally, lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gadoleic acid are present in the mixture in about the following percentages by weight, respectively: about 0.1% lauric acid, about 0.8% myristic acid, about 0.2% myristoleic acid, about 0.1% pentadecanoic acid, about 25.3% palmitic acid, about 7.2% palmitoleic acid, about 0.1% magaric acid, about 0.1% heptadecenoic acid, about 6.5% stearic acid, about 37.7% oleic acid, about 20.6% linoleic acid, about 0.8% linolenic acid, about 0.2% arachidic acid, and about 0.3% gadoleic acid.

In certain other embodiments, the fatty acid mixture of saturated and unsaturated fatty acids has a composition similar to lecithin. Lecithin (phosphatidylcholine) is a phosphatide found in all living organisms (plants and animals) and is a significant constituent of nervous tissue and brain substance. Lecithin is a mixture of the diglycerides of stearic acid, palmitic acid, and oleic acid, linked to the choline ester of phosphoric acid. The product of commerce is predominantly soybean lecithin obtained as a by-product in the manufacturing of soybean oil. Soybean lecithin contains by weight palmitic acid 11.7%, stearic acid 4.0%, palmitoleic acid 8.6%, oleic acid 9.8%, linoleic acid 55.0%, linolenic acid 4.0%, $C_{20}$ to $C_{22}$ acids (includes arachidonic acid) 5.5%. Lecithin may be represented by the formula: $C_8H_{17}O_5NR^9R^{10}$ wherein each of $R^9$ and $R^{10}$ are, independently, selected from the group consisting of stearic acid, palmitic acid, and oleic acid.

In certain other embodiments, the fatty acid mixture of saturated and unsaturated fatty acids has a composition similar to egg yolk. The composition (by weight) of the most prevalent fatty acid mixture in egg yolk can be broken into by weight:

A. unsaturated fatty acids such as oleic acid (about 47%), linoleic acid (about 16%), palmitoleic acid (about 5%), and linolenic acid (about 2%); and B. saturated fatty acids: such as palmitic acid (about 23%), stearic acid (about 4%), and myristic acid (about 1%).

Egg yolk is also a source of lecithin.

The above fatty acid mixtures (or fatty acid mixture sources) and percentages of fatty acids present in the various fatty acid mixture (or sources thereof) are provided as examples. The exact type of fatty acid present in the fatty acid mixture (or mixture sources) and the exact amount of fatty acid employed in the fatty acid mixture (or mixture sources) may be varied in order to obtain the result desired in the final product and such variations are now within the capabilities of those skilled in the art without the need for undue experimentation.

In certain embodiments of the present invention, the fatty acid mixture or fatty acid mixture source comprising at least 7, optionally at least 14, and optionally at least 22, unsaturated or saturated fatty acids selected from the group consisting of, but not limited to, butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, gadoleic acid, pentadecanoic acid, margaric acid, margaroleic acid, behenic acid, dihomolinoleic acid, arachidonic acid and lignoceric acid. Other useful fatty acids can be found in U.S. Pat. No. 4,874,794 to Adachi et al., herein incorporated by reference.

In certain embodiments, the fatty acid mixture in the admixture is obtained or sourced from oil mixtures. For example, cottonseed oil has a 2:1 ratio of polyunsaturated to saturated fatty acids. Its fatty acid profile generally consists of 70% unsaturated fatty acids including 18% monounsaturated (oleic), 52% polyunsaturated (linoleic) and 26% saturated (primarily palmitic and stearic). More specifically, cottonseed oil has fatty acids present in the mixture in about the following percentages by weight, respectively: about 0.5-2.0% myristic acid, about 17.0-29.0% palmitic acid, less than about 1.5% palmitoleic acid, about 1.0-4.0% stearic acid, about 13.0-44.0% oleic acid, about 40.0-63.0% linoleic acid, and about 0.1-2.1% linolenic acid.

Cocoa butter has fatty acids present in the mixture in about the following percentages by weight, respectively: at least about 0.1% myristic acid, about 0.5-26.3% palmitic acid, at least about 0.4% palmitoleic acid, about 0.5-33.8% stearic acid, about 0.5-34.4% oleic acid, and about 0.5-3.1% linoleic acid.

Olive oil was determined in one study to have fatty acids present in the mixture in about the following percentages by weight, respectively: about 0.5-9.0% palmitic acid, at least about 0.4% palmitoleic acid, about 0.5-2.7% of stearic acid, about 0.5-80.3% oleic acid, about 0.5-6.3% of linoleic acid, and about 0.5-0.7% linolenic acid.

Oils suitable for use as a fatty acid mixture source include, but are not limited to, *Adansonla digitata* oil; apricot (*Prunus armeniaca*) kernel oil; *Argania spinosa* oil; *Argemone mexicana* oil; avocado (*Persea gratissima*) oil; babassu (*Orbignya olelfera*) oil; balm mint (*Melissa officinalis*) seed oil; bitter almond (*Prunus amygdalus amara*) oil; bitter cherry (*Prunus cerasus*) oil; black currant (*Ribes nigrum*) oil; borage (*Borago officinalis*) seed oil; brazil (*Bertholletia excelsa*) nut oil; burdock (*Arctium lappa*) seed oil; butter; calophyllum tacamahaca oil; camellia kissi oil; camellia oleifera seed oil; canola oil; caraway (*Carum carvi*) seed oil; carrot (*Daucus carota sativa*) oil; cashew (*Anacardium occidentale*) nut oil; castor oil benzoate; castor (*Ricinus communis*) oil; cephalins; chaulmoogra (*Taraktogenos kurzii*) oil, chia (*Salvia hispanica*) oil; cocoa (*Theobrama cocao*) butter; coconut (*Cocos nucifera*) oil; cod liver oil; coffee (*Coffea arabica*) oil; corn (*Zea mays*) germ oil; corn (*Zea mays*) oil; cottonseed (*Gossypium*) oil; cucumber (*Cucumis sativus*) oil; dog rose (*Rosa canina*) hips oil; egg oil; emu oil; epoxidized soybean oil; evening primrose (*Oenothera biennis*) oil; fish liver oil; gevuina avellana oil; goat butter; grape (*Vitis vinifera*) seed oil; hazel (*Croylus americana*) nut oil; hazel (*Corylus aveilana*) nut oil; human placental lipids; hybrid safflower (*Carthamus tinctorius*) oil; hybrid sunflower (*Helianthus annuus*) seed oil; isatis tinctoria oil; job's tears (*Coix lacryma-jobi*) oil; jojoba oil; kiwi (*Actinidia chinensis*) seed oil; kukui (*Aleurites moluccana*) nut oil; lard; linseed (*Linum usitatissiumum*) oil; lupin (*Lupinus albus*) oil; macadamia nut oil; macadamia ternifolia seed oil; macadamia integrifolia seed oil; maleated soybean oil; mango (*Mangifera indica*) seed oil; marmot oil; meadowfoam (*Limnanthes fragraalba*) seed oil; menhaden oil; milk lipids; mink oil; moringa pterygosperma oil; mortierella oil; musk rose (*Rosa moschata*) seed oil; neatsfoot oil; neem (*Melia azadirachta*) seed oil; oat (*Avena sativa*) kernel oil; olive (*Olea europaea*) husk oil; olive (*Olea europaea*) oil; omental lipids; orange roughy oil; ostrich oil; oxidized corn oil; palm (*Elaeis guineensis*) kernel oil; palm (*Elaeis guineensis*) oil; passionflower (*Passiflora edulis*) oil; peach (*Prunus persica*) kernel oil; peanut (*Arachis hypogaea*) oil; pecan (*Caiya illinoensis*) oil; pengawar djambi (*Cibotium barometz*) oil; pistachio (*Pistacia vera*) nut oil; placental lipids; poppy (*Papaver orientale*) oil; pumpkin (*Cucurbita pepo*) seed oil; quinoa (*Chenopodium quinoa*) oil; rapeseed (*Brassica campestris*) oil; rice (*Oryza sativa*) bran oil; rice (*Oryza sativa*) germ oil; safflower (*Carthamus tinctorius*) oil; salmon oil; sandalwood (*Santalum album*) seed oil; seabuchthorn (*Hippophae rhamnoides*) oil; sesame (*Sesamum indicum*) oil; shark liver oil; shea butter (*Butyrospermum parkii*); silk worm lipids; skin lipids; soybean (*Glycine soja*) oil; soybean lipid; Sphingolipids; sunflower (*Helianthus annuus*) seed oil; sweet almond (*Prunus amygdalus dulcis*) oil; sweet cherry (*Prunus avium*) pit oil; tali oil; tallow; tea tree (*Melaleuca alternifolia*) oil; telphairia pedata oil; tomato (*Solanum lycopersicum*) oil; trichodesma zeylanicum oil; tuna oil; vegetable oil; walnut (*Juglans regia*) oil; wheat bran lipids; and wheat (*Triticum vulgare*) germ oil and mixtures thereof.

In certain embodiments, the oil is present in the compositions of the present invention in a total amount of from 0.01% (or about 0.01%) to 99.98% (or about 99.98%), or optionally 10% (or about 10%) to 90% (or about 90%), or optionally from 20% (or about 20%) to 70% (or about 70%), or optionally from 25% (or about 25%) to 50% (or about 50%), or optionally from 30% (or about 30%) to 40% (or about 40%), or optionally about 33%, by weight of the fatty acid mixture.

In certain embodiments the oil mixture used as a source of the fatty acid mixture is formed from oils selected to provide the following fatty acid composition: 0.3% (or about 0.3%) myristic acid, 19% (or about 19%) palmitic acid, 0.5% (or about 0.5%) palmitoleic acid, 13% (or about 13%) stearic acid, 44.4% (or about 44.4%) oleic acid, 21.3% (or about 21.3%) linoleic acid, and 0.5% (or about 0.5%) linolenic acid. In certain embodiments the oil mixture used as a source of the fatty acid mixture is formed from oils selected from the group consisting of cocoa butter, olive oil, cottonseed oil and mixtures thereof.

In certain embodiments, the fatty acid mixture or source of the fatty acid mixture is present in the compositions of the present invention in an amount from 0.01% (or about 0.01%) to 99.98% (or about 99.98%), or optionally 10% (or about 10%) to 90% (or about 90%), or optionally from 20% (or about 20%) to 70% (or about 70%), or optionally from 25% (or about 25%) to 50% (or about 50%), or optionally from 30% (or about 30%) to 40% (or about 40%), or optionally about 33%, by weight of the admixture.

In certain embodiments, the ratio of the acid component to the fatty acid mixture component on a weight/weight basis is from 0.01:1 (or about 0.01:1) to 1:0.01 (or about 1:0.01), optionally from 1:1 (or about 1:1) to 1:0.1 (or about 1:0.1), optionally from 1:1 (or about 1:1) to 1:0.5 (or about 1:0.5), or optionally, 1:1 (or about 1:1).

In certain embodiments, the ratio of the fatty acid mixture component to the antioxidant component on a weight/weight basis is from 0.01:1 (or about 0.01:1) to 1:0.01 (or about 1:0.01), optionally from 1:1 (or about 1:1) to 1:0.1 (or about 1:0.1), optionally from 1:1 (or about 1:1) to 1:0.5 (or about 1:0.5).

In certain embodiments, the ratio of the pyruvic acid component or the fatty acid mixture component to the antioxidant component on a weight/weight basis is from 1:1 (or about 1:1) to 1:0.01 (or about 1:0.01).

Without being limited by theory, the present inventors believe that the compositions and methods of the present invention provide improved hair growth or regrowth; provide a thicker or richer hair coat; and/or treat or prevent hair loss by accelerating the onset of the anagen phase of hair growth in mammals and/or increase the rate at which terminal hair appears on the skin of mammals.

Hair studies have concluded that the histological features of the human hair follicle vary extensively during the growth cycle. Hair can be classified as either: 1. terminal hairs which are darkly pigmented, long and thick or 2. vellus hair which very fine and light colored hair. In balding men thick terminal hair is often replaced by fine vellus-like hair.

All hair, terminal and vellus, goes through a growth phase (anagen), a regression or transitional phase (catagen), and a resting phase (telogen).

During the anagen phase, the growth cells in the dermal papilla rapidly divide and produce the hair shaft which becomes keratinized as it pushes up and out of the follicle into the pore. The anagen hair bulbs are located in the deeper subcutaneous fat levels of the skin. The catagen bulbs are in the dermis and telogen bulbs are in the mid-to-upper dermis.

The anagen phase for vellus hairs is typically much shorter than that for terminal hairs.

Optional Cosmetically Acceptable Active Agents

In one embodiment, the compositions according to this invention may further contain one or more additional cosmetically active agent(s) as well as the above-mentioned components. What is meant by a "cosmetically acceptable active agent" is a compound, which may be a synthetic compound or a compound isolated, purified or concentrated from a natural source, or a natural extract containing a mixture of compounds, that has a cosmetic effect on the tissue, including, but not limited to: anti-aging agents, sunscreens, photoprotectors, antioxidants, keratolytic agents, detergents/surfactants, moisturizers, nutrients, vitamins, minerals, energy enhancers, anti-perspiration agents, astringents, hair growth enhancing agents, hair coloring agents, pigments, firming agents, agents for skin conditioning, and odor-control agents such as odor masking or pH-changing and buffering agents.

In certain embodiments, the additional cosmetically acceptable active is a hair growth active selected from a group of compounds known to promote hair growth and available as drugs, such as minoxidil, diazoxide, pinacidil, bimatoprost, finasteride, a type 2 5-alpha-reductase inhibitor, and dutasteride, a type 1- and 2-5-alpha-reductase inhibitor, as well as flutamide, bicalutamide, pregnane derivatives, progesterone derivatives, experimental agents such as FCE 28260 and the like. Spironolactone and other diuretics may also be utilized as it is indicated for women in some cases (also known as aldactone: an aldosterone receptor antagonist).

In other embodiments of the compositions of the present invention, synthetic or natural 5-alpha-reductase inhibitors, or other anti-sebum ingredients including, but not limited to, sepicontrol (capryloyl glycine, sarcosine and cinamomum zeylanicum Bark Extract), licorice powder or extract, and the like may be incorporated. MC5 receptor antagonists may also be utilized in the compositions of this invention. Examples of MC5-R antagonists may be found in U.S. Pat. No. 7,049,331, herein incorporated by reference in its entirety.

Also useful in certain embodiments are herbal remedies that may have 5-alpha-reductase inhibitory action or otherwise induce hair growth may include: saw palmetto and *Pygeum africanum*. Other agents that may have such activity are beta-sisterol, sepicontrol and licorice, gamma-linolenic acid and other unsaturated fatty acids, zinc and zinc salts, *Cotinus coggygria* extract, green tea catechin (−)-epigallocatechin gallate (EGCG) and other polyphenols, and the like. Grape seed, apple seed, apple juice, and barley extracts may also be potential agents that may induce hair growth, although they are not thought to be very common or satisfactory in achieving satisfactory results.

Topical Carriers

The topical compositions useful in this invention contain formulations suitable for topical application to skin and scalp. The term "topical" as employed herein relates to the use of a composition along with a suitable pharmaceutical carrier, and applied according to the method of the present invention at the site of hair loss, reduced hair growth or baldness for exertion of local action. Accordingly, such topical compositions useful in the methods of the present invention include those pharmaceutical forms in which the compound is applied externally by direct contact with the skin surface to be treated.

In one embodiment, the compositions contain the above components in a cosmetically-acceptable topical carrier. Suitable carrier forms include ointments, pastes, gels, jellies, serums, aerosol and non-aerosol sprays, foams, creams, lotions, solutions, suspensions and the like. The term "ointment" embraces formulations (including creams) having oleaginous, absorption, water-soluble and emulsion-type bases, e.g., petrolatum, lanolin, polyethylene glycols, as well as mixtures of these. A more detailed discussion of the specific carriers and additional components useful in the compositions of the present invention can be found in U.S. Patent Publication 2008/0145331 to Bruning et al., herein incorporated by reference in its entirety. In one embodiment, the cosmetically-acceptable topical carrier constitutes from about 50% to about 99.99%, by weight, of the composition, or optionally, from about 80% to about 95%, by weight, of the composition.

Other Materials

Various other materials may also be present in the compositions useful in the subject invention. These include humectants, proteins and polypeptides, preservatives, an alkaline agent and mixtures thereof. The compositions of the present invention may also comprise chelating agents (e.g., EDTA) and preservatives (e.g., parabens). In addition, the topical compositions useful herein can contain conventional cosmetic adjuvants, such as dyes, sunscreen (e.g., titanium dioxide), pigments, and fragrances. A more detailed discussion of these and other materials can be found in previously incorporated U.S. Patent Publication 2008/0145331 to Bruning et al. as well as in U.S. Pat. No. 5,658,956 to Martin et al., which patent is herein incorporated by reference in its entirety.

Mixtures of the above preservatives can also be used.

Methods of Use

The use of compositions of this invention for accelerating the onset of the anagen phase of hair growth in a mammal and/or increasing the rate at which terminal hair appears on the skin by topical application of the present compositions was determined by the mice studies described below.

In certain embodiments, the compositions of this invention should be applied topically to the desired area of the mammalian or human body at least once per day for at least 11 weeks, optionally at least 9 weeks, or optionally at least 7 weeks. The hair growth benefits of the present invention may be maintained indefinitely by chronic administration of the compositions of the present invention.

EXAMPLES

The compositions of the present invention as described in following examples illustrate specific embodiments of compositions of the present invention, but are not intended to be limiting thereof. Other modifications can be undertaken by the skilled artisan without departing from the spirit and scope of this invention.

Determination of Accelerated Onset of Anagen Phase

To determine the acceleration in the onset of the anagen phase in the C3H mice, the following treatment formulations were prepared using conventional mixing technology.

| Ingredient | Treatment Formulation 1 | Treatment Formulation 2 | Treatment Formulation 3 | Treatment Formulation 4 | Treatment Formulation 5 | Treatment Formulation 6 |
|---|---|---|---|---|---|---|
| | Percent (w/w %) | | | | | |
| Water USP | 57.40 | 52.40 | 58.46 | 58.40 | 58.40 | 62.94 |
| Lactic Acid NF | 3.15 | 3.15 | 3.15 | 3.15 | 3.15 | 3.15 |
| Methylparaben NF | 0.20 | 0.20 | 0.20 | 0.20 | 0.20 | 0.20 |
| Minoxidil USP | — | 5.00 | 5.00 | 5.00 | 5.00 | 5.00 |
| Sodium Pyruvate | 7.00 | 7.00 | 7.00 | 1.00 | 7.00 | 3.50 |
| Polyoxyethylene (2) Stearyl Ether | 6.00 | 6.00 | 6.00 | 6.00 | 6.00 | 6.00 |
| Polyoxyethylene (20) Stearyl Ether | 6.00 | 6.00 | 6.00 | 6.00 | 6.00 | 6.00 |
| Cetearyl Alcohol (and) Ceteareth-20 | 6.00 | 6.00 | 6.00 | 6.00 | 6.00 | 6.00 |
| Propylparaben NF | 0.20 | 0.20 | 0.20 | 0.20 | 0.20 | 0.20 |
| Vitamin E Acetate NF | 7.00 | 7.00 | 7.00 | 7.00 | 1.00 | 3.50 |
| Cocoa Butter NF | 2.35 | 2.35 | 0.33 | 2.35 | 2.35 | 1.17 |
| Olive Oil NF | 2.35 | 2.35 | 0.33 | 2.35 | 2.35 | 1.17 |
| Cottonseed Oil NF | 2.35 | 2.35 | 0.33 | 2.35 | 2.35 | 1.17 |
| Citric Acid or Sodium Hydroxide | as needed | — | as needed | as needed | as needed | as needed |
| pH | 4.4 | 4.5 | 4.4 | 4.4 | 4.5 | 4.4 |

Treatment Formulation 7
(Actavis Minoxidil Topical Solution 5%)[1]

| Ingredients | Percent (w/w %) | pH |
|---|---|---|
| Water USP | N/A | Apparent pH = 8.1 |
| Propylene Glycol | N/A | |
| Alcohol | N/A | |
| Minoxidil USP | 5.00 | |

[1] Supplied by Actavis MidAtlantic LLC, Baltimore, MD.

C3H female mice at 6-7 weeks of age were purchased from Taconic Farms (Germantown, N.Y.). C3H mice's hair growth cycles have similar anagen, catagen and telogen phases. (Table 1) (Miyamoto I.; Hamada K., Journal of Dermatological Science, Volume 10, Number 1, July 1995, pp. 99-99(1)).

TABLE I

| | Weeks after Birth | | | | | |
|---|---|---|---|---|---|---|
| | Week 0 | Week 2 | Week 3 | Week 4 | Week 6 | Week 7 | Week 15 |
| Hair Growth Stage | Morphogenesis | Catagen | Telogen | Anagen | Catagen | Telogen | Anagen |

Each phase is much shorter and synchronized. This makes C3H mice a useful model for studying the induction activity of hair re-growth by active substances. C3H mice have a long telogen window from week 7 to week 15. Therefore, typically hair regrowth studies start at week 7 and end at week 15, i.e. the duration of a study is about 8 weeks.

Mice were housed in appropriately sized cages in an environmentally controlled room with a 12-hour light-12-hour dark photoperiod and supplied with food and water ad libitum. Animal care was based on the "Guide for the Care and Use of Laboratory Animals", NIH Publication No. 85-23. Once all mice entered their prolonged telogen/resting phase of the hair cycle, they were clipped over the dorsal area about 1.5×5 cm (Wahl Clippers 8900 Series, Blade #1086). Five female mice per group were clipped while sedated with 2% induction and maintenance isoflurane and 0.5 L Oxygen. The actual number of mice represented in the data may vary due to inadvertent death of one or more mice during study.

The treatment groups and treatment formulations were selected as follows:

| Group | Treatment Formulation |
|---|---|
| A | Test Formulation 1 (The admixture [7:7:7] w/o minoxidil) |

-continued

| Group | Treatment Formulation |
|---|---|
| B | Test Formulation 2 (The admixture [7:7:7] w/ 5% minoxidil) |
| C | Test Formulation 3 (The admixture [7:7:1] w/ 5% minoxidil) |
| D | Test Formulation 4 (The admixture [1:7:7] w/ 5% minoxidil) |
| E | Test Formulation 5 (The admixture [7:1:7] w/ 5% minoxidil) |
| F | Test Formulation 6 (The admixture [3.5:3.5:3.5] w/ 5% minoxidil) |
| G | Test Formulation 7 (5% minoxidil w/o the admixture) |
| H | No Treatment |

(the brackets "[ ]" indicate the w/w % ratio of the alpha-keto acid component to the antioxidant component to the fatty acid mixture component in the treatment formulation.)

200 mg of each test formulations were applied topically to the test skin area daily, 5 days a week. Images were taken on day 5 of each week of treatment and every 7 days thereafter to determine by visual observation the first signs of anagen/active growth phase and to determine rate at which terminal hairs cover skin treatment area. A study log (or, Anagen Phase Log) documenting day-to-day observations of mice entering anagen (grey skin, the first visual clue to a new hair growth) were recorded. Treatments continued for 9 weeks. Surprisingly, the onset of the anagen phase occurred faster in C3H mice groups treated with 5% minoxidil plus admixture of the present invention than with 5% minoxidil alone. The results recorded in the Anagen Phase Log are reproduced in Table II.

Table II indicates anagen phase onsets for Groups A-H as recorded in the anagen phase log.

TABLE II

| Group | Treatment Formulation | Anagen Phase Onset (Treatment Day) |
|---|---|---|
| A | Test Formulation 1 (The admixture [7:7:7] w/o minoxidil) | 19 |
| B | Test Formulation 2 (The admixture [7:7:7] w/ 5% minoxidil) | 15 |
| C | Test Formulation 3 (The admixture [7:7:1] w/ 5% minoxidil) | 15 |
| D | Test Formulation 4 (The admixture [1:7:7] w/ 5% minoxidil) | 15 |
| E | Test Formulation 5 (The admixture [7:1:7] w/ 5% minoxidil) | 11 |
| F | Test Formulation 6 (The admixture [3.5:3.5:3.5] w/ 5% minoxidil) | 14 |
| G | Test Formulation 7 (5% minoxidil w/o the admixture) | 24 |
| H | No Treatment | 42 |

(the brackets "[ ]" indicate the w/w % ratio of the alpha-keto acid component to the antioxidant component to the fatty acid mixture component in the treatment formulation.)

The data in Table II demonstrates that the onset of anagen phase occurred 5 days earlier in Group A than in Group G and 23 days earlier than in Group H. The addition of minoxidil to the admixture accelerated the onset of the anagen phase as follows:
  i. 9 days earlier in Groups B, C and D than in Group G and 27 days earlier than in Group H;
  ii. 13 days earlier in Group E than in Group G and 31 days earlier than in Group H.

The average degree of terminal hair coverage across mice in each Group was determined by visual inspection of the images taken at weeks 0, 4 and 5. The phrase "degree of terminal hair coverage", means the observed average estimated percentage of the treated site which is covered by terminal hair. The phrase "higher degree of terminal hair coverage" means the average terminal hair coverage associated with one group of mice is: a.) thicker or darker in color on average; and/or b.) covers a larger average observed estimated percentage of the treated site than is observed in another group. The phrase "low degree of terminal hair coverage" means the average terminal hair coverage associated with one group of mice is: a.) thinner or lighter in color on average; and/or b.) covers a less of an average observed estimated percentage of the treated site than is observed in another group. The phrase "faster degree of terminal hair coverage" means that a degree of terminal hair coverage is achieved faster in time. The term "average" means the average across the mice in each group. The term "observed" or "visual observations" means visual examinations of the images as carried out by the unaided human eye.

The groups were then ranked in order of highest degree of terminal hair coverage to lowest degree of terminal hair coverage. The admixture ratio of acid to antioxidant to fatty acid mixture for an indicated admixture component is described as in the brackets [ ] following the term "admixture".

Visual observation of images taken at week 0 (day that mice were shaved) demonstrated that, at this stage of the study, all the mice of Groups A-H had all terminal hair removed.

Table III is a ranking of the degree of terminal hair coverage for groups A, G and H based on images taken at week 5.

TABLE III

| Group | Week 5 Ranking: Degree of Terminal Hair Coverage (lowest number corresponding to highest degree of coverage) |
|---|---|
| A | 2 |
| G, H | 3 |

The ranking in Table III demonstrates that Group A treated with Formulation 5 (the admixture [7:7:7] without minoxidil)) provided faster and a higher degree of terminal hair coverage than untreated Group G and Group H treated with Formulation 7 (5% minoxidil alone).

It was further determined that addition of minoxidil to admixture provided an even faster and higher degree of efficacy. Based on the images taken at week 4, the Groups were ranked by degree of terminal hair coverage in Table IV.

TABLE IV

| Group | Week 4 Ranking: Degree of Terminal Hair Coverage (lowest number corresponding to highest degree of coverage) |
|---|---|
| E | 1 |
| B, C, D, F | 2 |
| A, H, G | 3 |

The ranking in Table IV demonstrates that Group E treated with Formulation 4 (5% minoxidil with the admixture [7:1:7]) provided the fastest and highest degree of terminal hair coverage of all the Groups—a week earlier than Group A treated with Formulation 5 (the admixture [7:7:7] without minoxidil). Groups B, C, D and F treated with Formulation 1 (5% minoxidil with the admixture [7:7:7]); Formulation 2 (5% minoxidil with the admixture [7:7:1]); Formulation 3 (5% minoxidil with the admixture [1:7:7]); and Formulation 6 (5% minoxidil with the admixture [3.5:3.5:3.5]), respectively, was second in providing the fastest and highest degree of terminal hair coverage of all the Groups. The Group A treated with Formulation 5 (the admixture [7:7:7] without minoxidil); untreated Group G and Group H treated with Formulation 7 (5% minoxidil without admixture) provided the least degree of terminal hair coverage at this stage of the study.

A summary of the ranking data recorded in Tables III and IV indicate that:
  a. mice skin treated with compositions containing the admixture without minoxidil demonstrated a faster degree of terminal hair coverage than non-treated mice skin
  b. mice skin treated with compositions containing the admixture where the ratio of alpha-keto acid to fatty acid mixture was 1:1, yet proportionally less antioxidant demonstrated a faster degree of terminal hair coverage than the admixture containing comparably lower amounts of the alpha-keto acid or the fatty acid mixture (i.e., given 1:1 ratios of antioxidant to fatty acid mixture and alpha-keto acid to antioxidant, respectively).
c. mice skin treated with compositions containing minoxidil and the admixture of the present invention demonstrated a faster degree of terminal hair coverage than:
  i. mice skin treated with compositions containing the equal amounts of minoxidil without the admixture;
  ii. mice skin treated with compositions containing the equal amounts of the admixture without minoxidil and
  iii. non-treated mice skin;

The following non-limiting examples further illustrate the compositions of the present disclosure. The ingredients in each example are prepared by mixing together the referenced ingredients using conventional mixing technology.

What is claimed is:
1. A hair regrowth composition, comprising
a. at least one hair growth active selected from the group consisting of minoxidil, diazoxide, pinacidil, bimatoprost, finasteride, dutasteride, synthetic or natural 5-alpha-reductase inhibitor, flutamide, bicalutamide, sepicontrol, MC5-R antagonist, aldosterone receptor antagonist, saw palmetto, *Pygeum africanum*, beta-sisterol, licorice, gamma-linolenic acid, zinc and zinc salts, *Cotinus coggygria* extract, green tea catechin (−)-epigallocatechin gallate (EGCG) at a safe and effective amount to grow or regrow hair; and
b. from about 0.1% to about 99% of an admixture, comprising:
  i. from about 0.01% to about 99.98% by weight of the admixture of an acid selected from the group con-

Hair Growth/Regrowth

| INCI Name | Trade Name | Example 1 (Lotion) % (w/w) | Example 2 (Lotion) % (w//w) | Example 3 (Cream) % (w//w) | Example 4 (Serum) % (w/w) | Example 5 (Lotion) % (w/w) | Vendor |
|---|---|---|---|---|---|---|---|
| Water | Water USP | 60.15 | 66.15 | 64.65 | 79.21 | 65.65 | |
| Lactic Acid | Purac PF 90 | 0.5 | — | — | — | — | PURAC, Inc. |
| Sodium Pyruvate | Sodium Pyruvate NF | 7.0 | 1.0 | 7.0 | 7.0 | 7.0 | Torary Industries, Inc. |
| Cocoa Butter | Cocoa Butter | 2.35 | 2.35 | 2.35 | 0.33 | 2.35 | Newtown Foods USA |
| Olive Oil | Olive Oil | 2.35 | 2.35 | 2.35 | 0.33 | 1.35 | Ventura Food, LLC |
| Cottonseed Oil | Cottonseed Oil | 2.35 | 2.35 | 1.35 | 0.33 | 2.35 | Ventura Food, LLC |
| Vitamin E Acetate | Vitamin E Acetate | 7.00 | 7.00 | 1.00 | 1.00 | 7.00 | BASF |
| Methylparaben | Methylparaben NF | 0.2 | 0.2 | 0.2 | 0.2 | 0.2 | ISP |
| Propylparaben | Propylparaben NF | 0.1 | 0.1 | 0.1 | 0.1 | 0.1 | Tri-K Industries |
| Polyoxyethylene (2) Stearyl Ether | Brij 72 | 6 | 6 | 6 | 6 | 6 | ICI |
| Polyoxyethylene (20) Stearyl Ether | Brij 78 | 6 | 6 | 6 | 3 | 6 | ICI |
| Cetyl Alcohol | Cetyl Alcohol | 6 | 6 | 8 | 2 | — | Henkel Co. |
| Xanthan Gum | Xanthan Gum | — | — | 0.5 | 0.5 | 1.0 | CPKelco |
| Veegum | Veegum | — | 0.5 | 0.5 | — | 1.0 | CPKelco |
| pH | | 3-7 | 3-7 | 3-7 | 3-7 | 3-7 | |

Hair Growth/Regrowth Serums

| INCI Name | Trade Name | Example 6 (Lotion) % (w/w) | Example 7 (Lotion) % (w/w) | Example 8 (Lotion) % (w/w) | Vendor |
|---|---|---|---|---|---|
| Water | Water USP | 51.00 | 56.00 | 60.95 | |
| Lactic Acid | Purac PF 90 | 5.15 | 5.15 | 5.15 | PURAC, Inc. |
| Minoxidil | Minoxidil | 10.0 | — | — | Pfizer |
| Finasteride | Finasteride | — | 5.0 | — | Merck |
| Bimatoprost | Bimatoprost | — | — | 0.05 | Allergan |
| Sodium Pyruvate | Sodium Pyruvate NF | 7.0 | 7.0 | 7.0 | Torary Industries, Inc. |
| Cocoa Butter | Cocoa Butter | 2.35 | 2.35 | 2.35 | Newtown Foods USA |
| Olive Oil | Olive Oil | 2.35 | 2.35 | 2.35 | Ventura Food, LLC |
| Cottonseed Oil | Cottonseed Oil | 2.35 | 2.35 | 2.35 | Ventura Food, LLC |
| Vitamin E Acetate | Vitamin E Acetate | 7.00 | 7.00 | 7.00 | BASF |
| Methylparaben | Methylparaben NF | 0.2 | 0.2 | 0.2 | ISP |
| Propylparaben | Propylparaben NF | 0.1 | 0.1 | 0.1 | Tri-K Industries |
| Polyoxyethylene (2) Stearyl Ether | Brij 72 | 6 | 6 | 6 | ICI |
| Polyoxyethylene (20) Stearyl Ether | Brij 78 | 6 | 6 | 6 | ICI |
| Xanthan Gum | Xanthan Gum | 0.5 | 0.5 | 0.5 | CPKelco |
| pH | | 3-7 | 3-7 | 3-7 | | sisting of intermediates of the Kreb cycle, non-Kreb cycle intermediate alpha-keto acid, derivatives thereof and mixtures thereof;

ii. from about 0.01% to about 99.98% by weight of the admixture of an antioxidant; and iii. from about 0.01% to about 99.98% by weight of the admixture of a fatty acid mixture or fatty acid mixture source comprising at least 7 unsaturated or saturated fatty acids selected from the group consisting of butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, gadoleic acid, pentadecanoic acid, margaric acid, margaroleic acid, behenic acid, dihomolinoleic acid, arachidonic acid and lignoceric acid.

* * * * *